US012494280B2

(12) United States Patent
Hoffmann et al.

(10) Patent No.: US 12,494,280 B2
(45) Date of Patent: Dec. 9, 2025

(54) MEDICAL IMAGING SYSTEM AND COMPUTER PROGRAM

(71) Applicant: Otto-von-Guericke-Universität Magdeburg, Magdeburg (DE)

(72) Inventors: Thomas Hoffmann, Magdeburg (DE); Daniele Passaretti, Magdeburg (DE); Robert Frysch, Welsleben (DE); Tim Pfeiffer, Magdeburg (DE); Georg Rose, Magdeburg (DE)

(73) Assignee: OTTO-VON-GUERICKE-UNIVERSITAT, Magdeburg (DE)

( * ) Notice: Subject to any disclaimer, the term of this patent is extended or adjusted under 35 U.S.C. 154(b) by 391 days.

(21) Appl. No.: 18/030,568

(22) PCT Filed: Oct. 5, 2021

(86) PCT No.: PCT/EP2021/077351
§ 371 (c)(1),
(2) Date: Apr. 6, 2023

(87) PCT Pub. No.: WO2022/073958
PCT Pub. Date: Apr. 14, 2022

(65) Prior Publication Data

US 2023/0377720 A1 Nov. 23, 2023

(30) Foreign Application Priority Data

Oct. 7, 2020 (EP) .................................... 20200500

(51) Int. Cl.
*G16H 30/20* (2018.01)
*G16H 30/40* (2018.01)

(52) U.S. Cl.
CPC ............ *G16H 30/20* (2018.01); *G16H 30/40* (2018.01)

(58) Field of Classification Search
None
See application file for complete search history.

(56) References Cited

U.S. PATENT DOCUMENTS 9,545,232 B2 1/2017 Noordhoek
2008/0103834 A1* 5/2008 Reiner .................. G16H 20/40 705/3

(Continued)

FOREIGN PATENT DOCUMENTS

DE 102018220758 A1 6/2020
EP 2903527 8/2015

(Continued)

OTHER PUBLICATIONS

International Search Report from corresponding International Patent Application No. PCT/EP21/77351, dated Dec. 13, 2021.

(Continued)

*Primary Examiner* — Dov Popovici
(74) *Attorney, Agent, or Firm* — RENNER, OTTO, BOISSELLE & SKLAR, LLP

(57) ABSTRACT

A medical imaging system repeatedly irradiates a capturing area of a patient with a radiation, acquires data from the irradiated area of the patient and generates images from such acquired data. The system is arranged for automatic adaptive adjustment of at least one parameter of the system influencing the image quality of the generated images dependent from the position, spatial orientation and/or type of an intervention tool which is introduced into the patient.

6 Claims, 4 Drawing Sheets

(56) References Cited

U.S. PATENT DOCUMENTS

| | | | | |
|---|---|---|---|---|
| 2015/0272531 | A1* | 10/2015 | Kieft ........................ | A61B 6/06 378/147 |
| 2015/0279031 | A1 | 10/2015 | Cavusoglu et al. | |
| 2020/0170752 | A1* | 6/2020 | Tashenov ............... | A61B 6/504 |
| 2020/0275982 | A1 | 9/2020 | Thienphrapa et al. | |

FOREIGN PATENT DOCUMENTS

| | | | |
|---|---|---|---|
| JP | 2005-525891 | A | 9/2005 |
| JP | 2013-542019 | A | 11/2013 |
| JP | 2015-530207 | A | 10/2015 |
| JP | 2018033818 | A | 3/2018 |
| JP | 2020-081858 | A | 6/2020 |
| WO | WO03/098245 | A1 | 11/2003 |
| WO | WO2012/056386 | A1 | 5/2012 |
| WO | WO2014/053970 | A1 | 4/2014 |

OTHER PUBLICATIONS

European Office Action issued in related European Patent Application No. 21 789 647.1 dated Jan. 29, 2025.

Office Action (with English translation) mailed Apr. 2, 2024 from related/corresponding Japanese Patent Appl. No. 2023-519320.

* cited by examiner

MEDICAL IMAGING SYSTEM AND COMPUTER PROGRAM

FIELD OF THE INVENTION

The invention is related to medical imaging systems and procedures for gathering images of areas of a patient, in particular of areas located inside the body of the patient. More particularly, the invention is related to a computer program and a medical imaging system which repeatedly irradiates a capturing area of a patient with a radiation and acquires data from the irradiated area of the patient and generates images from such acquired data. More specifically, the invention is related to the area of medical imaging during an operation, so called intervention, at the patient, which means the area of imaging guided interventions with an interventional tool such as an ablation device or a biopsy needle.

BACKGROUND OF THE INVENTION

In U.S. Pat. No. 9,545,232 B2, an interventional computer tomography application with movement needle detection and CT movement for improving needle artifact is known.

SUMMARY OF THE INVENTION

A device and method in accordance with the present invention can improve a medical imaging system for interventional procedures both for the patient and the operator. More particularly, a medical imaging system in accordance with the invention is arranged for automatic adaptive adjustment of at least one parameter of the system influencing the image quality of the generated images dependent from the position, spatial orientation and/or type of an interventional tool which is introduced into the patient. The invention is related to an adaptive image quality adjustment for therapeutic image sequences based on local structural information of a patient. In the current state of the art, in interventional minimally invasive therapy procedures, image quality is adjusted by the operator itself, e.g. by changing the tube current of a CT X-ray tube. There are no objective criteria for a sufficient image quality during CT imaging.

In standard diagnostic CT imaging there are various methods for modulating the dose within an image data acquisition. Most popular method is an online current modulation based on a calculation of the image noise ratio in the image raw data of the detector. If noise is too high the dose of the 180° projection is increased. Since diagnostic images need a constantly high quality for diagnosis, dose needs to be relatively high.

In interventional CT imaging the requirements regarding image quality are different. CT imaging is not used for doing a full diagnostic scan of a patient; it is used for positioning a medical instrument (such as a needle, or therapy applicator) in a target region, e.g. a tumor.

Unlike the diagnostic imaging method, in interventional CT there are just a few slices needed in which the needle tip is located. But those slices must be live updated, what means up to more than e.g. 5 frames per second.

It has been recognized that in most medical imaging systems which use radiation on the patient, for optimum image quality high radiation doses are required. While this might be necessary for standard diagnostic imaging, for example in CT diagnostic procedures, it has been found that this is not required during the whole interventional procedure. During significant parts of the interventional procedure, a significantly reduced image quality is sufficient for guiding the interventional tool from a start position to a target position in the body of a patient. For example, close to the start position or when the target position is reached, a very low image quality is sufficient. When the interventional tool passes risky areas in the body of the patient, then a higher image quality is required.

In accordance with aspects of the invention, the image quality can be controlled in real time during an interventional procedure according to the position, spatial orientation and/or type of the interventional tool. For example, when a type of interventional tool is used which has no sharp edges, then during the major part of the intervention procedure a low image quality might be sufficient. If an interventional tool with sharp edges, like a needle, is used, then sometimes a higher image quality is required, for example for passing the risky areas.

Similarly, the image quality can be controlled depending upon the position and/or spatial orientation of the interventional tool. The position can be defined relative to the distal end of the interventional tool which shall be guided to the target position.

Since the invention allows for reducing the image quality during significant parts of the interventional procedure, the radiation dose, which cause a radiation burden on the patient, can also be reduced. As a result, the system allows for dose reduction by adaptive image quality adjustment by dose modulation procedures during imaging guided interventions.

This allows for an autonomous feedback loop system for image quality adjustment based on data identifying the position, spatial orientation and/or type of an interventional tool.

According to an advantageous embodiment of the invention, it is proposed that the system is arranged for adaptive adjustment of the image quality by influencing the radiation dose irradiated by the system on the patient. It is advantageous that the radiation dose can be influenced by several different parameters. This gives a large freedom for implementation of such adaptive adjustment of the image quality.

According to an advantageous embodiment of the invention, it is proposed that the system is arranged for adaptive adjustment of the image quality by influencing one, several or all of the following parameters of the system:

a) Tube current,
b) Tube voltage,
c) Size of the irradiated area of the patient,
d) Position of the irradiated area of the patient,
e) Number of projections (per rotation),
f) Exposure time.

The angle of irradiation can be defined in a CT system by the actual rotation angle of the X-ray tube.

According to an advantageous embodiment of the invention, it is proposed that the areas of high and low image quality are defined by a predetermined database or online by a feedback decision model (e.g. Al based). Thus, the areas of high and low image quality can be planned before an interventional procedure at a patient is started. For example, the planning of the path of the interventional tool in the patient and the areas of high and low image quality can be planned using standard diagnostic imaging, for example, CT imaging before the interventional procedure is started.

According to an advantageous embodiment of the invention, it is proposed that the system is arranged for varying the image quality several times from a start position to a target position during the introduction of the interventional tool into the patient. As a result, only the required image quality is applied at the several stages of an interventional procedure. For example, the radiation dose can be modulated according to the image quality needs to fulfill these goals.

According to an advantageous embodiment of the invention, it is proposed that the system is arranged for reducing the image quality when the interventional tool reaches the target position. This has the advantage that the patient as well as the operator can be exposed to high dose radiation only during short time intervals, while introducing the interventional tool, but during longer time periods when the interventional work (e.g. local application of energy for therapeutic purpose) is done at the target position, the radiation dose can be reduced.

According to an advantageous embodiment of the invention, it is proposed that the system is arranged for automatic adaptive adjustment of the image quality as a function of a previously calculated path that the interventional tool is to be moved in the patient from the start position to the target position. This has the advantage that the data of the previously calculated path of the interventional tool can be used also for dose modulation of the radiation. The calculation of the path is required anyway for doing the interventional procedure.

According to an advantageous embodiment of the invention, it is proposed that the system is arranged for increasing the image quality at predefined risk positions lying on the path of the interventional tool from the start position to the target position. For example, such risk positions or risk structures can be arteries or nerves.

In some stages of the interventional tool positioning process the image quality can be low since there are just soft tissue structures with no risk of violating risk structures. A low image quality means for example: high noise, high artifacts (e.g. metal artifacts by the interventional tool). But some stages of the interventional tool path can be very near to risk structures. For this a higher image quality is needed. Image quality can be expressed by one or more of several influencing parameters, like image resolution, image noise, artifacts, image sharpness and number of images per second (frame rate). If image quality is to be reduced, resolution can be reduced, and/or noise can be increased, and/or artifacts can be increased, and/or image sharpness can be decreased, and/or the frame rate can be reduced.

A computer program is also provided for adaptively adjusting the image quality in an medical imaging system which repeatedly irradiates a capturing area of a patient with a radiation and acquires data from the irradiated area of the patient and generates images from such acquired data, wherein the computer program is arranged for performing the following steps when the computer program is executed on a computer of the system:

a) Inputting at least one value identifying the position, spatial orientation and/or type of an interventional tool which is introduced into the patient,
b) Calculating, as a function of the inputted value, an adjustment value by which an adaptive adjustment of at least one parameter of the system influencing the image quality of the generated images can be carried out,
c) Outputting the adjustment value to at least one control component of the system which allows the adjustment of at least one parameter of the system influencing the image quality of the generated images.

With such computer program the same advantages can be achieved as mentioned before. The several functions of the system which are mentioned before can also be implemented in the computer program as further program steps.

For example, the computer program can be arranged for inputting characteristic values of a pre-calculated path in which the interventional tool is to follow in the patient from the start position to the target position and for calculating the adjustment value depending on the characteristic values.

The computer can be any commercially available computer, like a PC, Laptop, Notebook, Tablet or Smartphone, or a microprocessor, microcontroller or FPGA, or a system-on-chip (SoC) or a combination of such elements.

The system can work in addition with a dose saving approach called "Volume of Interest Imaging" (VOI). Within this approach the problem is addressed that there is no need for having image information about the patient's whole body. There is just an area needed which represents the interventional tool path from insertion to target. This VOI imaging can be realized using active collimator leaves in x- and z-direction which absorb the radiation in areas outside the VOI. The missing information of projection data (called truncated image data) can be partially compensated by model assumptions or prior information of the patient's body. This VOI method is worse for image quality but has a high potential for dose reduction during minimally invasive imaging guided interventions.

Further features:

- A system that images the path of a device, e.g. needle, in a patient from an insertion point to an end point
- The system automatically adjusts its image quality depending on the path point that was calculated before
- Areas of high and low image quality are defined by a pre operative planning scan with automatic or manual risk structure detection
- The system automatically adjusts its image quality depending on the topology, location and orientation of the inserted device for avoiding artifacts
- The system automatically adjusts image quality by increasing or decreasing the X-ray dose. Dose can be modulated by:
  - Changing the tube current
  - Changing the tube voltage
  - Changing the exposure time
  - Changing the number of projections
  - Changing the irradiated volume
- The operator (physician) can adjust a mean, minimum and maximum image quality (boundary conditions), but the system can do it automatically too.

BRIEF DESCRIPTION OF THE DRAWINGS

The invention is further described using exemplary embodiments and drawings. The drawings show in FIG. 1 a schematic illustration of a conventional percutaneous intervention and FIG. 2 a VOI image of the three stages of FIG. 1 and FIG. 3 the interaction of a computer program with the medical imaging system and FIG. 4 a CT system with a tube in two different positions and FIG. 5 a medical imaging system with automatic image quality adjustment.

DETAILED DESCRIPTION OF THE INVENTION

Figure 1:
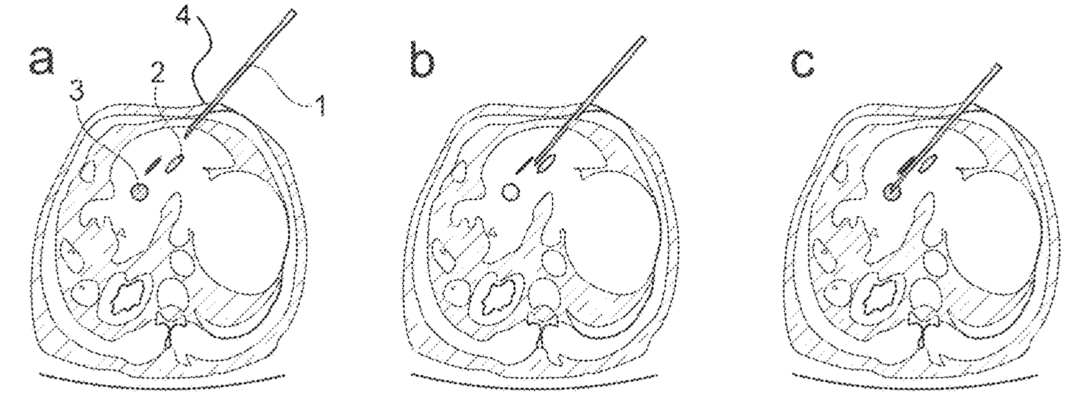

FIG. 1 shows three stages of a conventional percutaneous (in plane) intervention with permanent CT imaging. An interventional tool 1, for example a needle, is introduced into a patient. The distal end of the interventional tool 1 follows a previously calculated path from a start position 4 to a target position 3, where a target structure, for example a tumor, is located. On this path some risk positions 2, for example nerves or arteries, need to be considered. In order to avoid damage on these risk structures, the interventional tool 1 needs to be guided very carefully. This requires a high image quality at least in the area of the risk structures 2.

In FIG. 1*a*, the distal end of the interventional tool 1 is at the start position 4. In FIG. 1*b*, the distal end of the interventional tool 1 has reached the risk position 2. In FIG. 1*c*, the distal end of the interventional tool 1 has reached the target position 3.

Figure 2:
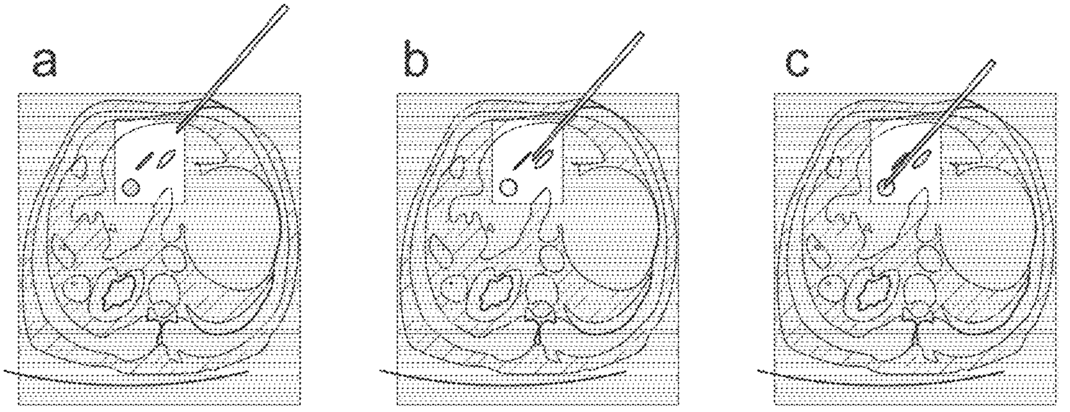

FIG. 2 shows the same interventional procedure as depicted in FIG. 1 and the same three stages a, b, c. In FIG. 2 the automatic adaptive adjustment of at least one parameter of the system which influences the image quality of the generated image is applied. In this case, the size of the image is reduced to a volume of interest. FIG. 2*a* shows the interventional tool after insertion in a region with low risk and low demands on image quality, therefore a low radiation dose is used. FIG. 2*b* shows the interventional tool in a region with high demands to the accuracy because of the risk structures at risk position 2. Image quality is automatically increased by an increased radiation dose. FIG. 2*c* shows that the interventional tool hit the target structure at target position 3. Therefore, image quality can be decreased again, for example by reducing the radiation dose.

Figure 3:
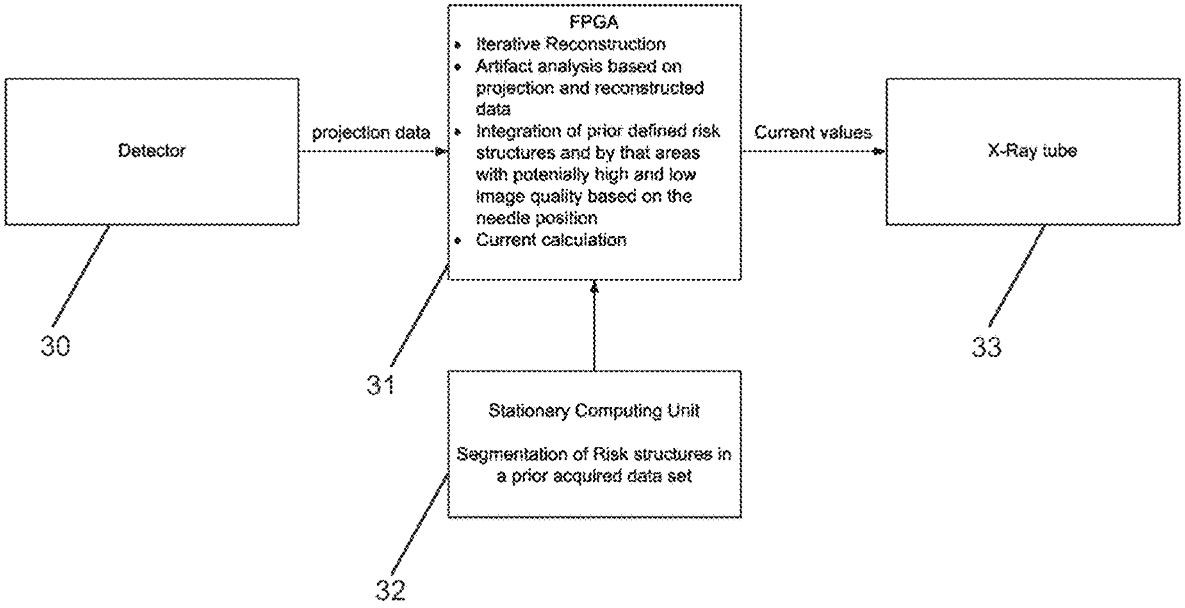

FIG. 3 shows an example for embedding a computer program for adaptively adjusting the image quality in the medical imaging system, for example by implementing the computer program in an FPGA. The medical imaging system comprises a detector 30 and a radiation source 33, for example an X-ray tube. The detector can be an X-ray detector, as it is used in CT systems. The system further comprises a stationary computing unit 32 and an additional computing unit 31 in the form of an FPGA. The stationary computing unit 33 provides data defining the segmentation of risk structures in a prior acquired data set of the patient. The detector 30 provides projection data from the patient to the computing unit 31. The computing unit 31 can perform the following steps:

- Iterative reconstruction
- Artifact analysis based on projection and reconstructed data
- Integration of prior defined risk structures and by that areas with potentially high and low image quality based on the interventional tool position
- Decision feedback system algorithm for dose modulation (by prior described methods)

The computing unit 31 calculates current values for the current of the radiation source 33 and sends them to a control unit which controls the radiation source 33. By modulating the current of the radiation source 33, the radiation dose can be adjusted according to the invention. As a result, the image quality is modulated according to the quality needs of the different positions of the interventional tool within the patient.

Figure 4:
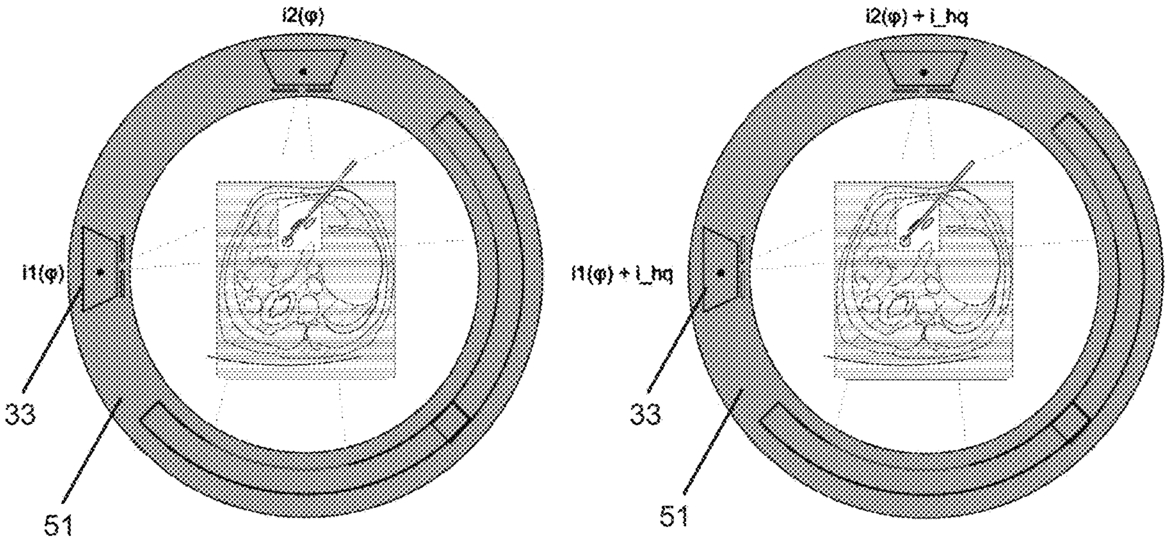

FIG. 4 shows the medical imaging system with the radiation source 33 in two different positions. The radiation source 33 can be mounted to a gantry 51 which performs the rotational movement around the patient. A current modulation of the radiation source 33 is basically always possible due to the irregular form of the patient depending on the rotating angle of the tube. The right picture shows additional quality modulated current for high image quality in a region of interest.

Figure 5:
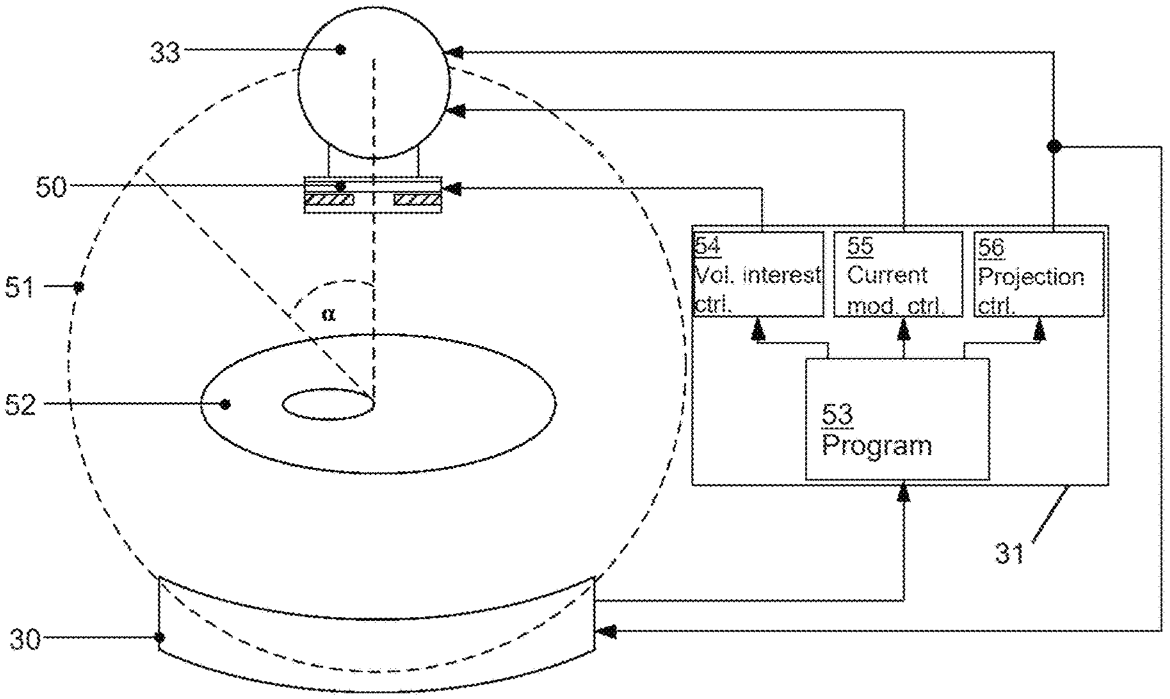

FIG. 5 shows a medical imaging system having a radiation source 33, for example a X-ray tube, a collimator 50, a gantry 51, a radiation detector 30 and a computing unit 31. Further, there is some space for placing a patient 52 with the target structure for the interventional procedure. The radiation source 33 provides the radiation to the patient through the collimator 50. By means of the collimator 50 the size and position of the irradiated area of the patient 52 can be controlled. The gantry 51 can be rotated around the patient 52, for example at an angle α. The radiation source 33 and the collimator 50 are mounted to the gantry 51 and therefore can be rotated in the same way. Further, the detector 30 is also mounted on the gantry 51 and therefore is rotated in the same way as the radiation source 33 and the collimator 50.

The computing unit 31, for example a FPGA, comprises a computer program 53 with several algorithms. Further, the computing unit 31 comprises a volume of interest control section 54 which controls the collimator 50. Further, the computing unit 31 comprises a current modulation control section 55 which provides control to the actual current of the radiation source 33. In addition, the computing unit 31 comprises a projection control section 56 which controls the number of projections and the projection angle done by the radiation source 33 and the detector 30.

Similar to FIG. 3, the detector 30 provides projection data to the computing unit 31. Further, additional information about the interventional tool 1 can be provided to the computing unit 31 through an additional interface.

In the computer program 53 several algorithms are performed, for example an artifact evaluation, a noise evaluation and an automatic adaptive adjustment of the image quality, for example by dose modulation of the radiation dose of the radiation source 33. The computer program 53 provides input data to the control sections 54, 55, 56.

The volume of interest control section 54 controls the collimator 50, for example by providing different shutter positions depending on the rotation angle α. The current modulation control section 55 provides current values for controlling the current of the radiation source 33. The projection control section 56 provides acquisition parameters and active angular positions to the gantry control, the radiation source 33 and the detector 30.

What is claimed is:

1. A medical imaging system which repeatedly irradiates a capturing area of a patient with a radiation and acquires data from the irradiated area of the patient and generates images from such acquired data, wherein the system is configured for automatic adaptive adjustment of at least one parameter of the system influencing an image quality of the generated images dependent from a position, spatial orientation and/or type of an interventional tool which is introduced into the patient, wherein the system is configured for varying the image quality several times from a start position to a target position during the introduction of the interventional tool into the patient, wherein the system is configured for automatic adaptive adjustment of the image quality as a function of a previously calculated path that the interventional tool is to travel in the patient from the start position to the target position, wherein the system is configured for increasing the image quality at predefined risk positions lying on the path of the interventional tool from the start position to the target position, and wherein the system is configured for reducing the image quality when the interventional tool reaches the target position.

2. The system according to claim 1, wherein the system is configured for adaptive adjustment of the image quality by influencing a radiation dose irradiated by the system on the patient.

3. The system according to claim 1, wherein the system is configured for adaptive adjustment of the image quality by influencing one, several or all of the following parameters of the system:

a) tube current, b) tube voltage, c) size of the irradiated area of the patient, d) position of the irradiated area of the patient, e) number of projections (per rotation), f) exposure time.

4. The system according to claim 1, wherein areas of high and low image quality are defined by a predetermined database.

5. The system according to claim 1, wherein a computer program is stored on a non-transitory computer readable medium of the medical imaging system for adaptively adjusting the image quality in the medical imaging system which repeatedly irradiates a capturing area of the patient with the radiation and acquires data from the irradiated area of the patient and generates images from such acquired data, wherein the computer program is configured for performing the following steps when the computer program is executed on a computer of the system:

a) inputting at least one value identifying the position, spatial orientation and/or type of an interventional tool which is introduced into the patient, b) calculating, as a function of the inputted value, an adjustment value by which an adaptive adjustment of at least one parameter of the system influencing the image quality of the generated images can be carried out, c) outputting the adjustment value to at least one control component of the system which allows the adjustment of at least one parameter of the system influencing the image quality of the generated images.

6. The system according to claim 5, wherein the computer program is configured for inputting characteristic values of a pre-calculated path which the interventional tool is to follow in the patient from the start position to the target position and for calculating the adjustment value depending on the characteristic values.

* * * * *